United States Patent [19]
DeSavigny

[11] 3,959,464
[45] May 25, 1976

[54] MICROENCAPSULATED METHYL AND ETHYL PARATHION INSECTICIDE IN AQUEOUS CARRIER

[75] Inventor: Chester Blair DeSavigny, Malvern, Pa.

[73] Assignee: Pennwalt Corporation, Philadelphia, Pa.

[22] Filed: June 3, 1971

[21] Appl. No.: 149,816

[52] U.S. Cl................................. 424/78; 424/32; 424/218
[51] Int. Cl.².......................................... A01N 9/36
[58] Field of Search...................... 424/32, 78, 218

[56] References Cited
UNITED STATES PATENTS

| 3,074,845 | 1/1963 | Geary | 424/32 X |
|---|---|---|---|
| 3,212,967 | 10/1965 | McFadden et al. | 424/78 |
| 3,577,515 | 5/1971 | Vandegaer | 424/32 |

*Primary Examiner*—Leonard Schenkman

[57] ABSTRACT

Microcapsules of methyl parathion or ethyl parathion contained within a wall of cross-linked polyamide-polyurea are improved insecticidal compositions having more effective and extended toxicity to insects and decreased toxicity to mammals. The compositions are stable in aqueous carriers.

3 Claims, No Drawings

MICROENCAPSULATED METHYL AND ETHYL PARATHION INSECTICIDE IN AQUEOUS CARRIER

This invention concerns an improved insecticidal composition comprising microcapsules, desirably admixed in an aqueous carrier, of O,O-dimethyl-O-p-nitrophenol phosphorothioate or O,O-diethyl-O-p-nitrophenol phosphorothioate contained within an encapsulating polymer skin material consisting of cross-linked polyamide-polyurea.

O,O-dimethyl-O-p-nitrophenol phosphorothioate (known and referred to hereinafter as "methyl parathion") and O,O-diethyl-O-p-nitrophenol phosphorothioate (known and referred to hereinafter as "ethyl parathion") are well-known, highly toxic, non-persistent insecticides. One of the disadvantages of the use of methyl and ethyl parothion as insecticides is their rapid degradation in the field, believed to be caused by hydrolysis and oxidation reactions. (See Graetz et al., "Water Pollution Control Federation" 42 (2) Part 2, pp. R-76-92, February 1970). Accordingly, in ordinary methods of application, methyl and ethyl parathion are pesticidally effective in the field for a period of only several days. Another major disadvantage of previous methods of using methyl and ethyl parathion as insecticides is the danger to wildlife, domestic animals, and humans because of these compounds' extreme toxicity to mammals.

In contrast, the reduced toxicity of the encapsulated parathions of this invention to animals is indeed striking. Specifically, the toxicity of encapsulated methyl parathion is only one-tenth that of the unencapsulated methyl parathion, while the toxicity of encapsulated ethyl parathion to mammals is only one-hundredth that of the unencapsulated ethyl parathion composition. It is thus a surprising aspect of this invention that although the encapsulated parathions are significantly less toxic to mammals than the unencapsulated parathions, the encapsulated parathions are more toxic to insects than the unencapsulated material, showing a more effective kill at smaller concentrations, in addition to killing insects for an extended period of time in the field, for example, up to eight days or more insecticidal effectiveness for the encapsulated composition at dosage concentrations of 0.25 to 1 lb/acre of the parathions, compared to only about one day of effectiveness at concentrations of 1 lb/acre for unencapsulated parathions. The encapsulated parathions thus give a more effective insect control than the unencapsulated material at equivalent concentrations.

The use of the previously known parathion compositions also presented a serious pollution problem, as well as a safety hazard to field workers since repeated applications with the fast-degrading pesticides were necessary, thereby increasing the danger to the field workers caused by the insecticides' high mammalian toxicity by either oral ingestion or skin contact. These hazards are substantially eliminated by the present invention because of the need for fewer applications of a less concentrated insecticide (in the encapsulated form) and, as mentioned above, the markedly reduced mammalian toxicity of the encapsulated product. With regard to alleviation of pollution hazards, it has been discovered that the encapsulated parathions do not filter into the soil in contrast to the unencapsulated insecticides which filter into the soil to a depth of at least 4 to 6 inches. The encapsulated parathions therefore do not present a hazard to deep soil inhabitants, such as earthworms, and are not washed through the soil to contaminate streams, rivers and lakes.

Another major disadvantage of unmodified, unencapsulated methyl and ethyl parathions is their limited use capability because of their chemical phytotoxicity to various food crops. In contrast, the encapsulated parathions embodied in this invention can be used to protect crops from insect infestation without causing damage to the plants. This unexpected result of the present invention of reducing the herbicidal effects of the insecticides extends the fields of use of the parathions immeasurably.

The present invention provides an improved insecticidal composition, having the advantages and alleviating the problems as above discussed, comprising microcapsules comprised of methyl parathion or ethyl parathion contained within an encapsulating wall or skin of cross-linked polyamide-polyurea. A preferred and unexpected embodiment of the invention is the admixture of said microcapsules in aqueous carrier, i.e., a slurry, suspension, or dispersion of the microcapsules in water, which may have included therein suspending agents, for example, cross-linked acrylic acid interpolymers as discussed in U.S. Pat. No. 3,426,004, other suspending agents such as hydroxyethyl cellulose, gums, clays, sub-micron size silica and other inorganic materials; wetting agents and dispersants such as detergents, polyvinyl alcohols, gelatin, methyl cellulose, casein and clays; and "stickers" (materials which will cause the capsules to stick onto the foliage and not drop to the ground) such as gelatin, bentonites, gums, polysulfides, polyacrylic acid, and both petroleum and animal oils.

The polymerization method and technique of preparing microcapsules embodied in this invention are described in the patent of J. E. Vandegaer, U.S. Pat. No. 3,577,515, May 4, 1971, and the corresponding British Pat. No. 1,091,141 published Nov. 15, 1967. Described in these references is a process of encapsulation by interfacial condensation of complementary, organic, polycondensate-forming intermediates which react to form cross-linked, polyamide-polyurea polycondensate which comprises: establishing, by agitation, a dispersion of to-be-encapsulated droplets containing a first of said intermediates, in a body of liquid which is in continuous phase and is immiscible with the droplets and is essentially free of any reactant complementary to said first intermediate, and (2) thereafter bringing a second of said intermediates, i.e., complementary to the first intermediate, into the continuous liquid phase so that the first and second intermediates react as interfaces between the droplets and the continuous phase to encapsulate the droplets with a skin of said polycondensate, at least one of said first and second intermediates comprising at least in part a polyfunctional reactant which (a) is complementary to and effective for cross-linking reaction with the other of said first and second intermediates and (b) has at least three reactive groups that are the same as each other and are effectively functional in said polycondensate-forming reaction, and that are selected from the class consistig of amine, isocyanate, —COCl and —SO₂Cl groups, said first and second intermediates thereby reacting to encapsulate the droplets within the aforesaid polycondensate skin having cross-linking therein. Examples of suitable diamine and polyamine reactants are ethylene diamine, phenylene diamine, toluene diamine, hexamethylene diamine, diethylene triamine, piperazine, 1,3,5-benzenetriamine trihydrochloride, 2,4,6-triaminotoluene trihydrochloride, tetraethylene pentamine, pentaethylene hexamine, polyethylene imine, 1,3,6-triaminonaphthlene, 3,4,5-triamino-1,2,4-triazole, melamine, and 1,4,5,8-tetraminoanthraquinone. Examples of difunctional and polyfunctional acid derived compounds providing —COCl and —SO$_2$Cl reactive groups are sebacoyl chloride, ethylene-bis-chloroformate, phosgene, azelaoyl chloride, adipoyl chloride, terephthaloyl chloride, dodecanedioic acid chloride, dimer acid chloride, 1,3-benzene sulfonyl dichloride, trimesoyl chloride, 1,2,4,5-benzene tetraacid chloride, 1,3,5-benzene trisulfonyl chloride, trimer acid chloride, citric acid chloride and 1,3,5-benzene trischloroformate. Intermediates useful in providing reactive isocyanate groups are represented by such compounds as para-phenylene diisocyanate, meta-phenylene diisocyanate, naphthalene-1,5-diisocyanate, tetrachloro-m-phenylene diisocyanate, 2,4-toluene diisocyanate, 2,6-toluene diisocyanate, 4,4-diphenyl diisocyanate, the dichloro diphenyl methane diisocyanates, bibenzyl diisocyanate, bitolylene diisocyanate, the diphenyl ether diisocyanates, the dimethyldiphenyl diisocyanates, the polymethylene polyphenyl isocyanates, triphenylmethane-4,4',4''-triisocyanate, isopropylbenzene α-diisocyanate and the like.

Sufficient polyfunctional reactant (i.e., trifunctional or greater), e.g., a reactant having at least 3 functional groups thereon as above-described, is provided in the polycondensation recipe to produce microcapsules wherein the polyamide-polyurea capsule wall is about 10 to 50% cross-linked, that is, 10 to 50% of the polymer is part of a three dimensional polymer network. In the preferred embodiments the polyamide-polyurea capsule wall will be 20 to 30% cross-linked. Microcapsules of polyamides with no cross linking would, graphically speaking, be made up of strands of linear polymer molecules not connected to eaach other. By cross linking the polyamide, these strands are linked together at various spots along their length making a much "tighter" network.

The average particle size of the microcapsules will generally range from about 30 to about 130 microns with a preferred average particle size of about 80 to 100 microns. Such relatively fine particles are advantageous to prevent plugging of orifices in the spraying equipment used for field application of the pesticide compositions. The wall thickness of the cross-linked, polyamide-polyurea capsule will range from about 0.5 micron to 4 microns, with from about 1 to 3 microns thickness preferred. The thickness of the capsule wall, as well as the degree of crosslinking of the polymer constituting same, will affect the rate of diffusion of the parathion insecticide therethrough, and thereby influence the performance of the insecticide in the field relative to extended life and insect kill rate. The microcapsule size thereof is controlled during the manufacturing process by such expedients as carefully monitoring the degree of dispersion of the material to be encapsulated by controlling the agitation and amount of emulsifying agent in the continuous phase. The microcapsule wall thickness is controlled by the quantity of the reactive intermediate dissolved in the material to be encapsulated.

A suspension or slurry of the microcapsules in water is the normal embodiment for shipping, storing, and ultimately dispensing the insecticide composition to the area to be protected from insect infestation. Conventional spraying apparatus is used for application of these insecticidal formulations. It is most surprising that the water suspensions and slurries of the encapsulated insecticide, the preferred embodiments of this invention, are operable in light of the knowledge that methyl and ethyl parathion are rendered ineffectual by hydrolysis when contacted by moisture. Indeed, it is significant that the suspensions and slurries of the encapsulated insecticide in water demonstrate good storage stability. For example, even after periods of storage of water suspensions of up to 6 to 12 months and longer, the effectiveness of the microcapsules in controlling insects is not materially decreased. For instance, after twelve months of storage only about a 10 percent drop in concentration of active methyl parathion in the encapsulated form in water dispersion is noted, not considered to be an appreciable loss.

The weight ratio of the pesticide to the polymer in the encapsulated composition will generally range from about 2:1 to 10:1 with a ratio of about 5:1 being preferred. A convenient water dispersion, suspension or slurry for shipping and storage will consist of from about 10 to 30% by weight, preferably about 25%, of the pesticide-containing microcapsules, which will be diluted to about 1% for spraying.

An exemplary recipe for preparing the cross-linked polyamide-polyurea encapsulating polymer wall for the methyl and ethyl parathion is as follows: Polyfunctional isocyanate (such as polymethylene polyphenylisocyanate known as "PAPI"): $x$ moles, where $x$ equals 0.1 to 0.5; Diacid chloride (such as sebacoyl dichloride): $1 - x$ moles; Difunctional amine (such as ethylene diamine): $n-y$ moles, where $n$ equals 1 to 3; Diethylene triamine (a difunctional polyamine): $y$ moles, where $y = 0$ to 1.5; in addition, $1 - x$ moles of sodium carbonate may be included in the recipe to neutralize the hydrochloric acid generated during the polycondensation reaction. Excess amine may be present in the recipe. The diacid chloride and isocyanate are added to the insecticide which acts as a water-insoluble organic solvent. The organic material is dispersed in water and the amine is charged to the reaction as an aqueous solution. The procedure of the aforementioned U.S. Pat. No. 3,577,515 is employed to produce the encapsulated parathion product.

EXAMPLE 1

The following solutions are prepared:

A. Stock solution of polyvinyl alcohol, a 4% aqueous solution of which has a viscosity of 35–45 cp. at 20°C. determined by Hoeppler falling ball method ("Elvanol 50 – 42 G," E. I DuPont de Nemours & Company) in warm water with high speed stirring.

B. Amine solution of
  14.6 g. ethylene diamine
  16.6 g. diethylenetriamine
  25.6 g. sodium carbonate, anhydrous
  200 ml. water C. Organic phase, prepared just prior to use.
  200 g. technical methyl parathion
  29.0 g. sebacyl chloride
  10.8 g. polymethylene polyphenylisocyanate ("PAPI," Upjohn Company)

| | |
|---|---|
| Isocyanate equivalent (dibutylamine) | 135 maximum |
| Viscosity (centipoises at 25°C.) | 400 maximum |
| Acid value (ppm of H+) | 200 maximum |

| -continued | |
|---|---|
| Volatile content (100% C./20 mm.) | 0.3% maximum |
| Specific gravity (20/20°C.) | 1.2 |
| Average molecular weight | 380 to 400 |
| Flash point (Cleveland Open Cup) | 425°F. |
| NCO content by weight | 31% minimum. |

600 ml. of 0.5% polyvinyl alcohol solution A is placed in a 2 liter baffled flask and stirred vigorously with a "Dispersator" unit (Premier Mill Corporation) equipped with a 1 inch duplex head. The organic phase, solution C, is added, followed immediately by amine solution B. A paddle stirrer is substituted for the dispersion stirrer and the mixture is agitated slowly to maintain suspension for 2 hours. The microcapsules are recovered by vacuum filtration, washed with water to a neutral pH, and redispersed in water to produce a slurried product containing the equivalent of 17% active methyl parathion.

A commercial methyl parathion concentrate is diluted and emulsified with water to provide a composition containing 10% active methyl parathion as control. Both materials are applied to cotton plants in the greenhouse at the same concentrations of 1 lb./acre active ingredient, using conventional spray equipment. At selected time intervals, 25 bollworms are placed on the treated leaves and the percentage kill noted. Encapsulated methyl parathion gives effective, long-lasting control (100% kill after 7 days and 75% kill after 10 days) while the control shows rapid decrease in activity (giving only about 5% kill after 7 days, and no kill after 10 days).

EXAMPLE 2

A similar experiment is conducted employing 100 boll weevils for each determination using a reduced dosage rate of 0.25 lb/acre of methyl parathion. After seven days the encapsulated product continues to give effective kill and control (at least 95 to 100% kill) whereas the unencapsulated methyl parathion is almost totally ineffective.

EXAMPLE 3

Bean foliage is sprayed in the greenhouse with a water dispersion of encapsulated methyl parathion (prepared as in Example 1) and with an unencapsulated emulsifiable concentrate control for testing against spider mites. Results are shown in Table 1 below. The encapsulated pesticide gives effective control for about 10 days at a dose rate of 0.5 lb/acre versus only 1 day for the control. Since spider mites do not ingest insecticide residues, it is evident that the active insecticide is slowly released through the capsule wall to kill by vapor and/or contact action. Moreover, the greenhouse environment which destroys the bioactivity of the unprotected methyl parathion control has a lesser effect on the encapsulated methyl parathion.

The results of the example demonstrate the unexpected finding that reduced dose rates may be used for the composition of the invention. Referring to Table 1, it is seen that 0.5 lb./acre of encapslated methyl paration gives better contrl than 1 lb./acre or even 5 lb./acre of commercial, unencapsulated methyl parathion. This finding provides an important economic advantage in the practice of the invention.

TABLE 1

Activity Against Two-Spot Spider Mites

| | Rate (active agent lbs/acre) | Percent Kill After | | | | | |
|---|---|---|---|---|---|---|---|
| | | 1 day | 3 days | 7 days | 10 days | 13 days | 19 days |
| Microcapsules of methyl parathion | 5 lb. | 100 | 100 | 100 | 100 | 100 | 75 |
| | 1 lb. | 50 | 100 | 100 | 100 | 99 | 50 |
| | 0.5 lb. | 25 | 90 | 100 | 100 | 95 | 25 |
| Methyl parathion, emulsion concentrate (E.C.) | 5 lb. | 100 | 100 | 100 | 75 | 50 | 0 |
| | 1 lb. | 90 | 100 | 50 | 25 | 0 | 0 |
| | 0.5 lb. | 50 | 50 | 0 | 0 | 0 | 0 |

(1) All formultions diluted in water. E.C. formulation contained 10% Me-Parathion, 5% "Triton X-155" emulsifier and 85% Xylene, in water.

EXAMPLE 4

Ethyl parathion is encapsulated with a cross-linked polyamide-polyurea wall as in Example 1 to produce a water slurry of microcapsules containing 17% active ingredient. Cotton seedlings are sprayed with this slurry at 0.2 lb. (active ingredient)/acre dose rate along with an unencapsulated control at the same dose rate. Kill of boll weevils placed on these treated seedlings is determined at various intervals as shown below.

| | % kill, days | | | | |
|---|---|---|---|---|---|
| | 1 | 2 | 4 | 6 | 8 |
| encapsulated ethyl parathion | 80 | 68 | 56 | 50 | 30 |
| unencapsulated ethyl parathion | 36 | 20 | 12 | 0 | 5 |

EXAMPLE 5

In outdoor tests on field plots, bean plants are sprayed with an aqueous slurry of encapsulated methyl parathion and a concentrate control of the insecticide at equal dose rates of 0.5 lb/acre using a No. 6510 nozzle with screens removed. The foliage is tested each day using crickets and Japanese Beetles as the test insects, with the following results:

| | % kill, days | | | | |
|---|---|---|---|---|---|
| | 1 | 2 | 3 | 4 | 5 |
| encapsulated methyl parathion | 100 | 100 | 100 | 100 | 100 |
| unencapsulated methyl parathion | 100 | 100 | 100 beetles 0 crickets | 0 | 0 |

EXAMPLE 6

Cotton plants in the field are sprayed with a water dispersion of encapsulated methyl parathion and with a methyl parathion concentrate at various and equivalent dose rates. A bioassay made on the treated leaves after three days using boll weevils as the subject pest shows the following results:

| | Rate, lb./acre | % kill |
|---|---|---|
| Encapsulated methyl parathion | ¼ | 100 |
| | ½ | 100 |
| Unencapsulated methyl parathion | ½ | 40 |

Again, the unexpected advantage of using lower dose rates with the encapsulated composition is demonstrated by the foregoing data.

EXAMPLE 7

The more persistent and more effective activity of the encapsulated parathions is demonstrated by a series of field tests as above, except that the plots are subjected to heavy rainfall. The insect killing effects of the compositions of this invention are not diminished, whereas the activity of the unmodified parathions is depleted by the moisture.

EXAMPLE 8

The more effective control of the gypsy moth on oak foliage by the encapsulated parathions at equivalent dose rates (1 lb. parathion/100 gal.) is shown by the following results:

| | % kill, days | | |
|---|---|---|---|
| | 4 | 9 | 32 |
| encapsulated methyl parathion | 100 | 100 | 87 |
| encapsulated ethyl parathion | 100 | 100 | 87 |
| unencapsulated methyl parathion | 48 | 0 | 0 |

EXAMPLE 9

Toxicity tests are carried out to demonstrate the relative and surprising safety of the compositions of this invention to mammals.

The acute oral toxicities of encapsulated samples and commercial, emulsifiable concentrate controls are determined on mice. Samples are administered by stomach tube without prior trituration. Results are presented in the following table:

| Sample | | $LD_{50}$ (in terms of active ingredient) | $LD_{50}$ (as is) |
|---|---|---|---|
| 1. | Unencapsulated methyl parathion (MP) (44% active) | 10 mg/kg | 23 mg/kg |
| 2. | Encapsulated MP (12% active) | 106 " | 860 " |
| 3. | Encapsulated MP (14% active) | 89 " | 620 " |
| 4. | Encapsulated MP (75% active) | 87 " | 115 " |
| 5. | Unencapsulated ethyl parathion (EP) (45% active) | 10 " | 22 " |
| 6. | Encapsulated EP (27% active) | 1460 " | 5600 " |
| 7. | Encapsulated EP (29% active) | 1380 " | 4800 " |
| 8. | Tissue-homogenized encapsulated EP (29% active) | 14 " | 50 " |

The above $LD_{50}$ values show that the encapsulated methyl parathion product has about 0.1 of the toxicity to mammals of the unencapsulated, emulsifiable concentrate control, and that the ethyl parathion capsule has about 0.01 the toxicity of the unencapsulated control. In sample No. 8 an encapsulated ethyl parathion is homogenized by tissue grinding and a typical $LD_{50}$ is exhibited.

Dermal toxicity on rabbits is determined by placing the test material in contact with non-abraided rabbit skin for 24 hours using standard dermal toxicity test procedures. With encapsulated methyl parathion in a water suspension (12–14% active ingredient), three rabbit deaths out of 21 at a dose rate of 2.25 g. active methyl parathion per kilogram of body weight are noted after 22 to 30 hours. A control with only 178 mg. methyl parathion per kilogram of body weight with unencapsulated emulsifiable concentrate (44% active) results in death after only 4.25 hours.

Encapsulated ethyl parathion in a water suspension is found to be nontoxic when applied to the skin of three rabbits. The dermal $LD_{50}$ for unencapsulated ethyl parathion concentrate control is, however, found to be 35 mg/kg based on active ethyl parathion.

I claim:

1. A storage-stable, sprayable, aqueous-based insecticidal composition consisting essentially of a mixture in water of microcapsules comprised of methyl or ethyl parathion contained within an encapsulating wall of cross-linked polyamide-polyurea, the parathion being diffusible therethrough, about 10 to 50% of the cross-linked polyamide-polyurea encapsulating wall being embodied in a three dimensional polymer network, the weight ratio of said parathion to the polyamide-polyurea of the microcapsule being in the range of about 2:1 to 10:1, and the concentration of the microcapsules in the aqueous mixture being from about 1 to about 30% by weight.

2. The composition of claim 1 wherein the average particle size of the microcapsules is within the range of about 80 to about 100 microns.

3. The composition of claim 1 wherein about 20 to 30% of the cross-linked polyamide-polyurea encapsulating wall is embodied in a three dimensional polymer network.

* * * * *